United States Patent [19]
Merritt et al.

[11] 3,962,357
[45] June 8, 1976

[54] PROCESS FOR THE PREPARATION OF SUBSTITUTED VINYLBENZYL CHLORIDE

[75] Inventors: Richard F. Merritt, Fort Washington, Pa.; Clark R. Carpenter, Berlin, N.J.

[73] Assignee: Rohm and Haas Company, Philadelphia, Pa.

[22] Filed: July 1, 1974

[21] Appl. No.: 484,634

[52] U.S. Cl.............. 260/651 R; 260/651 HA; 260/465 G; 260/515 A
[51] Int. Cl.².............. C07C 25/24; C07C 17/14
[58] Field of Search..... 260/651 R, 651 HA, 465 G, 260/515 A

[56] References Cited
UNITED STATES PATENTS

| 2,780,604 | 2/1957 | Clarke et al. | 260/651 R |
| 2,981,758 | 4/1961 | Hoffenberg | 260/651 R |
| 3,560,580 | 2/1971 | Burk | 260/651 R |

*Primary Examiner*—D. Horwitz

[57] ABSTRACT

An improved continous single step vapor phase process for the preparation of substituted vinylbenzyl chloride from substituted ethyltoluene is disclosed. In this process a substituted ethyltoluene is reacted with a halogen gas in the vapor phase, at elevated temperatures via a continuous feed process. Furthermore, this process achieves halogenation followed by dehydrohalogenation in a single pass through the reactor. There is also obtained a very high total selectivity to vinylbenzyl chloride and its precursors via this continuous process.

12 Claims, 1 Drawing Figure

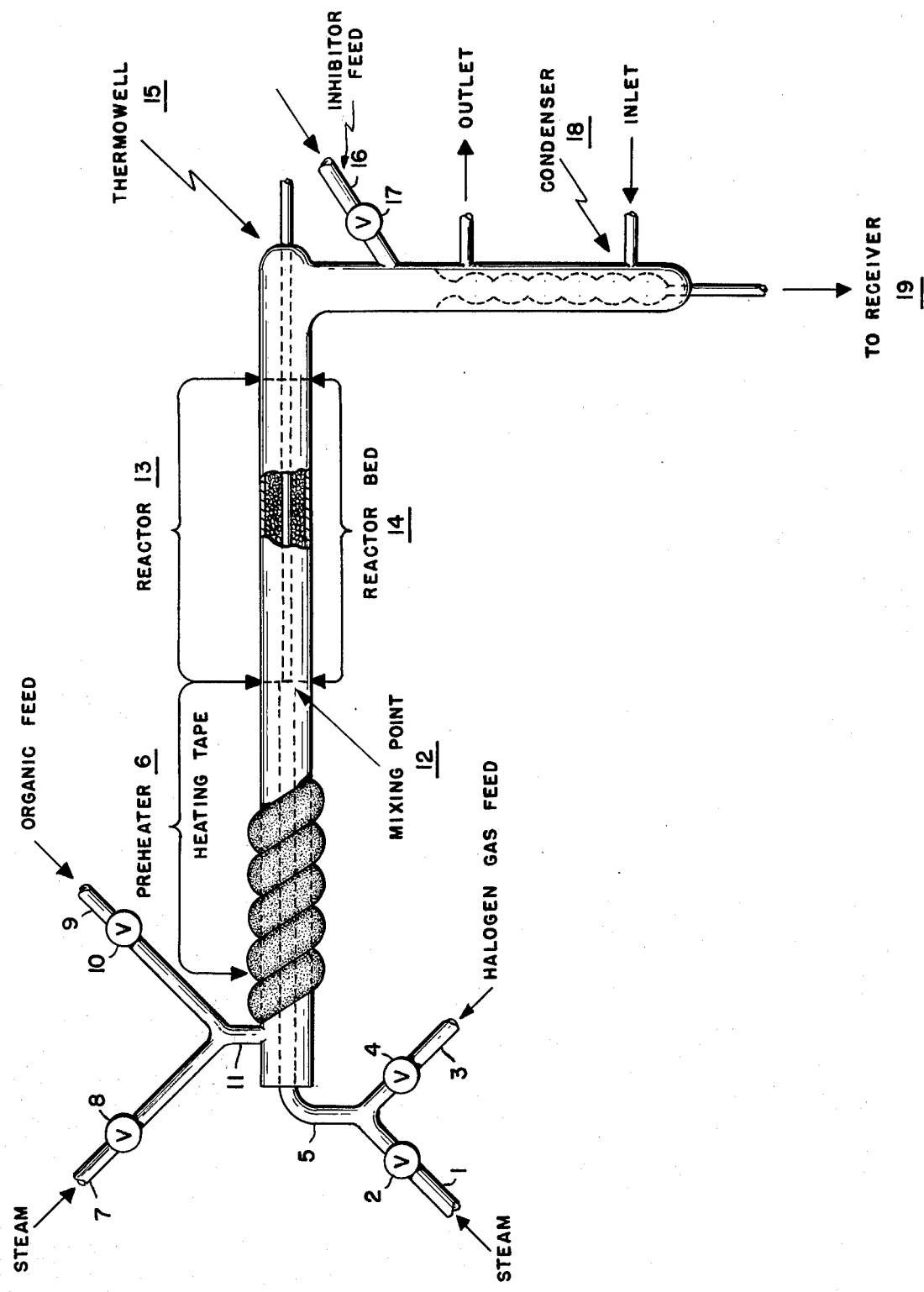

PROCESS FOR THE PREPARATION OF SUBSTITUTED VINYLBENZYL CHLORIDE

SUMMARY OF THE INVENTION

This invention describes a continuous high temperature vapor phase process for the preparation of substituted vinylbenzyl chloride from substituted ethyl toluene. In this process halogenation and subsequent dehydrohalogenation of substituted ethyltoluene to form substituted vinylbenzyl chloride is performed in the vapor phase, at elevated temperatures in a reactor bed preferably composed of silica particles. The amount of silica particles should be controlled so as to eliminate excessive back pressure. A polymerization inhibitor is added to the reaction product which is then condensed and collected. The substituted vinylbenzyl chloride is separated from by-products formed therewith by conventional techniques.

BACKGROUND OF THE INVENTION

It is well known in the art that at moderate temperatures and varying pressures chloromethylation of aromatic nuclei can be accomplished with formaldehyde and haloacids or with other chloromethylating agents in the presence of a suitable catalyst. These reactions are well known in the literature.

In U.S. Pat. No. 3,652,689 there is described a liquid phase chloromethylation process as shown below:

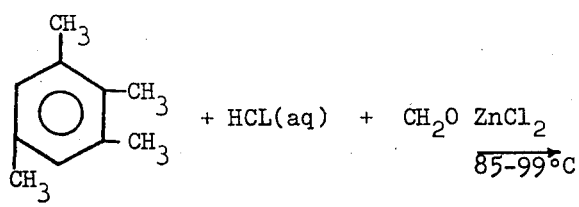

Described in U.S. Pat. No. 3,625,870 is a chloromethylation process using chloromethyl ether and zirconium tetrachloride which is also done in the liquid phase as shown below:

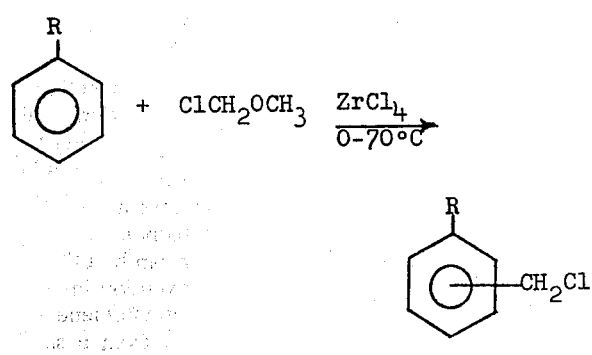

A process for the polychloromethylation of alkaryl hydrocarbons is disclosed in U.S. Pat. No. 3,422,160 as shown below:

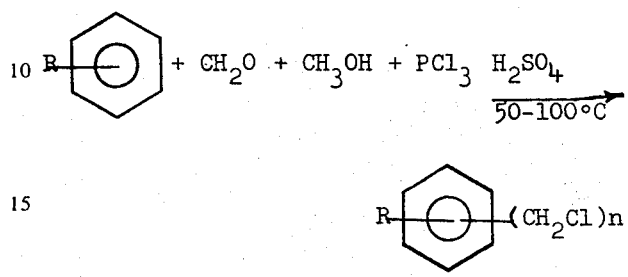

wherein the chloromethylating agent is produced by the reaction of formaldehyde and a halogen acid generating agent such as $PCl_3$.

Chloromethyl benzene has also been produced by the reaction of formaldehyde and halogen acid using sulfur compounds containing halogen as a catalyst, as shown in U.S. Pat. No. 3,271,465 below:

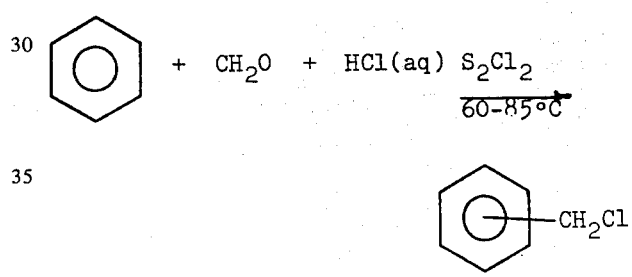

U.S. Pat. No. 2,973,891 describes a liquid phase chloromethylation of benzene using zinc chloride in the presence of an alkali metal or alkaline earth chloride as shown below:

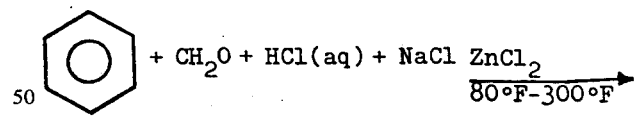

A selective monochloromethylation and dichloromethylation at varying pressures has been accomplished using formaldehyde and aqueous hydrochloric acid in the presence of zinc chloride as described in U.S. Pat. No. 2,951,100. It has been reported that various mixtures of $\alpha$- and $\beta$- chlorostyrenes and dichlorostyrenes can be prepared by the chlorination of styrenes via ultraviolet light and low temperatures as described in the work published by Sadykh-Zade et al. The art also describes in U.S. Pat. No. 2,981,758 the chlorination of alkyl vinyl aromatic compounds at relatively high temperatures without chlorinating the vinyl group as shown below:

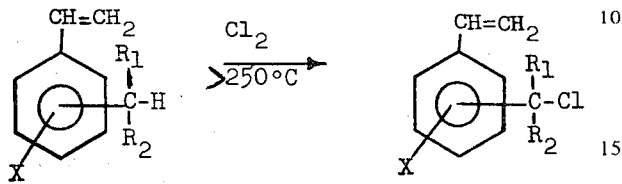

Finally the art teaches in U.S. Pat. No. 2,780,604 that chloromethyl vinyl benzene can be prepared via a two step liquid phase reaction whereby isopropyl toluene is chlorinated via ultraviolent light and the subsequently distilled chloromethyl chloroisopropyl benzene is dehydrohalogenated with heat to give chloromethylisopropenylbenzene.

None of the above patents disclose a continuous high temperature vapor phase process for the preparation of substituted vinylbenzyl chloride from substituted ethyl toluene.

The obvious advantages of this process are: the elimination of multiple steps in the preparation of the desired product, the high percentage of total selectivity to substituted vinylbenzyl chloride and its precursors, the ability to use a substituted ethyltoluene which is a much more stable molecule than a substituted vinyltoluene, the elimination of the need for a dehydrogenation step to produce the substituted vinyltoluene needed for the U.S. Pat. No. 2,981,758, the fact that the by-product produced along with the desired substituted vinylbenzyl chloride are all substituted vinylbenzyl chloride precursors and these precursors may be separated and recycled through the reactor to produce additional substituted vinylbenzyl chlorides.

DETAILS OF THE DRAWING

To illustrate the process of the present invention, reference is made to the accompanying drawing which shows diagrammatically a preferred procedure for practicing the invention as shown. In this preferred procedure steam is fed through line 1 and meter 2 and is combined with a halogen gas, which is fed through line 3 and meter 4, in line 5 and then enters the preheater 6. Steam is also fed through line 7 and meter 8 and is combined with the organic feed, which is fed through line 9 and meter 10, in line 11 and then enters the preheater. Line 5 is extended through the preheater to the mixing point 12 where the two steam streams combine just prior to entering the reactor 13. Inside the reactor, the two steam streams react on the reactor surface 14, where halogenation and dehydrohalogenation takes place. The temperature within the reactor 13 is monitored via the thermowell 15. The reaction product is then mixed with a polymerization inhibitor which is fed through line 16 and meter 17 and condensed in condenser 18 and collected in receiver 19. The reaction product is then separated from by-products by conventional procedures.

DETAILS OF THE INVENTION

A preferred embodiment of this invention is the novel continuous single step vapor phase process for the preparation of a substituted vinylbenzyl chloride which comprises contacting a substituted ethyl toluene of the formula:

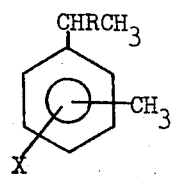

wherein R is a substituent selected from the group consisting of: hydrogen, chlorine, bromine and ($C_1$–$C_4$)alkyl and X is a substituted selected from the group consisting of: hydrogen, ($C_1$–$C_4$)-alkyl, halogen, cyano, aryl, hydroxy, carboxy and OY where Y is an aryl group, as a vapor with chlorine in the presence of a suitable reaction surface at a temperature of between 250°C. and 750°C., condensing the organic product and separating the halogenated reaction product from by-products formed therewith.

It is found that the more preferred reaction surface for this process consists of Vycor chips. Vycor is a high purity silica with a softening point ($T_m$) of approximately 1500°C. (see the Condensed Chemical Dictionary Van Norstrand Reinhold Co. N.Y., 8th Ed., (1971). However, other reaction surfaces such as glass helices, ceramic rings and charcoal pellets can also be used.

A more preferred temperature range used in this process is between 450°C. to 650°C, although temperatures above 250°C and less than 750°C can also be utilized.

A more preferred process for reacting the two reagents is by feeding them into two separate steam streams and allowing them to become intermixed just prior to entering the superheated reaction zone. In this manner the chlorination and subsequent dehydrohalogenation takes place in a single pass through the superheated silica reactor bed.

In accordance with this invention any inert diluent can be utilized in place of the steam to carry the vaporized aromatic reagents and the halogen gas to the mixing site. Examples of other inert diluents are carbon tetrachloride nitrogen, helium and argon. The reaction time for this process may be from 0.01 to 200 seconds depending on the rate of flow of the reagents through the reaction bed and the temperature employed; the more preferable reaction time being from 0.05 to 10 seconds.

In a more preferred embodiment of this invention a polymerization inhibitor is added to the reaction product either immediately before or after condensing the product as it comes out of the reactor bed. The inhibitors which are employed in this process are o-nitrophenol, o-nitrocresol, and t-butylcatechol. However, any phenolic polymerization inhibitor can be utilized.

A more preferred process of this invention involves recycling the unreacted substituted ethyltoluene and the substituted vinyltoluene recovered from a single pass through the reactor, thereby increasing the percentage of ethyltoluene conversion.

The more preferred pressures used in this process are from 0.1 to 2.0 atmospheres.

In this process the reaction can be performed utilizing isothermal as well as gradient temperatures.

In this process the relative amounts of substituted vinylbenzyl chloride and its precursors can be varied by changes in reactant mole ratio, reactant partial pressure, contact time, and the mixing and reaction temperatures.

The more preferred organic starting material is one selected from the group consisting of:
2-ethyltoluene, 3-ethyltoluene, 4-ethyltoluene
2-ethyl-3-methyltoluene, 2-ethyl-4-methyltoluene
2-ethyl-5-methyltoluene, 2-ethyl-6-methyltoluene
3-ethyl-2-methyltoluene, 3-ethyl-4-methyltoluene
3-ethyl-5-methyltoluene, 4-ethyl-2-methyltoluene
4-ethyl-3-methyltoluene, 5-ethyl-2-methyltoluene,
2,3-diethyltoluene, 2,4-diethyltoluene,
2,5-diethyltoluene, 2,6-diethyltoluene,
3,4-diethyltoluene, 3,5-diethyltoluene
2-(chloroethyl)toluene, 3-(chloroethyl)toluene,
4-(chloroethyl)toluene, 2-(chloroethyl)-3-methyltoluene, 2-(chloroethyl)-4-methyltoluene,
2-(chloroethyl)-5-methyltoluene, 2-(chloroethyl)-6-methyltoluene, 3-(chloroethyl)-2-methyltoluene,
3-(chloroethyl)-4-methyltoluene, 3-(chloroethyl)-5-methyltoluene, 4-(chloromethyl)-2-methyltoluene
4-(chloroethyl)-3-methyltoluene, 5-(chloroethyl)-2-methyltoluene, 2,3-di(chloroethyl)toluene
2,4-di(chloroethyl)toluene, 2,5-di(chloroethyl) toluene, 2,6-di(chloroethyl)toluene, 3,4-di(chloroethyl)toluene, 3,5-di(chloroethyl)toluene,
2-(bromoethyl)toluene, 3-(bromoethyl)toluene,
4-(bromoethyl)toluene, 2-(bromoethyl)-3-methyltoluene, 2-(bromoethyl)-4-methyltoluene,
2-(bromoethyl)-5-methyltoluene, 2-(bromoethyl)-6-methyltoluene, 3-(bromoethyl)-2-methyltoluene,
3-(bromoethyl)-4-methyltoluene, 3-(bromoethyl)-4-methyltoluene, 3-(bromoethyl)-5-methyltoluene,
4-(bromoethyl)-2-methyltoluene, 4-(bromoethyl)-3-methyltoluene, 5-(bromoethyl)-2-methyltoluene,
2,3-di(bromoethyl)toluene, 2,4-di(bromoethyl)toluene, 2,4-di(bromoethyl)toluene, 2,5-di(bromoethyl)toluene, 2,6-di(bromoethyl)toluene,
3,4-di(bromoethyl)toluene, 3,5-di(bromoethyl)toluene.

In order to further illustrate the invention the following examples are presented, however, these examples are not to be considered as limiting embodiments of the invention.

EXAMPLE 1

A reactor is constructed as shown in the diagram. Superheated steam is fed at a constant rate of 4.45 mole/hr. through two Vycor tubes acting as a preheater to the desired reaction temperature, in this particular case, 560°C. The ethyltoluene is fed to the outer steam stream before the preheater at 0.68 mole/hr. while chlorine is mixed with the inner stream at 0.36 mole/hr. After mixing the two separate flows, the chlorinations and dehydrochlorination of the ethyltoluene take place in the reaction zone, which is packed with Vycor chips, with a contact time of approximately 0.5 sec. After emerging from the reaction zone the stream is condensed, inhibited, and the organic material separated from the aqueous solution. The organic material can be purified and the vinylbenzyl chloride recovered at this point or, alternatively, the organic mixture recycled to the reactor for increased ethyltoluene conversion.

Under the above conditions, a single passage of the reactants through the vapor phase chlorinator results in 32% conversion of the ethyltoluene. Selectivity to vinylbenzyl chloride amounts to 13%. Other vinylbenzyl chloride precursors and their selectivity of formation are vinyltoluene (33%), ethylbenzyl chloride (24%), α-chloroethylbenzyl chloride (2%), and α-chloroethyltoluene (1%). Thus, total selectivity to vinylbenzyl chloride and its precursors amounts to 73%. The relative amounts of vinylbenzyl chloride and precursors can be varied by changes in reactant mole ratio, reactant partial pressure, contact time, and the mixing and reaction temperatures.

EXAMPLE II

Reactants are fed to the reactor described in the accompanying drawing at the following rates:

| total steam | 428 | g/hr. |
|---|---|---|
| ethyltoluene | 88.8 | g/hr. |
| chlorine | 35.5 | g/hr. |

Conditions are established such that the residence time in the reactor zone is 0.4 seconds at 557°C (isothermal). At an ethyltoluene conversion of 56%, the total yield of vinylbenzyl chloride and its precursors is 89% (based on unrecovered ethyltoluene):

| | |
|---|---|
| ethylbenzyl chloride | 42.0% |
| vinyltoluene | 33.5% |
| vinylbenzyl chloride | 12.7% |
| Chloroethyltoluene | 0.2% |
| chloroethylbenzyl chloride | 0.3% |
| Total | 88.7% |

EXAMPLE III

Under conditions indentical to Example 1, except that the temperature profile is staged from 520°C at the mixpoint to 616°C at the end of the reactor zone, the following results are obtained at an ethyltoluene conversion of 55%, the total yield of vinylbenzyl chloride and its precursors is 89% (yield based on unrecovered ethyltoluene):

| | |
|---|---|
| ethylbenzyl chloride | 42.1% |
| vinyltoluene | 34.0% |
| vinylbenzyl chloride | 12.3% |
| chloroethyltoluene | 0.1% |
| chloroethylbenzyl chloride | 0.3% |
| Total | 88.8% |

We claim:

1. A continuous, single step vapor phase process for the preparation of a substituted vinylbenzyl chloride which comprises contacting a substituted ethyl toluene of the formula:

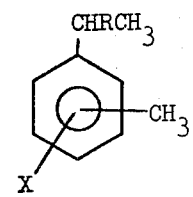

wherein R is a substituent selected from the group consisting of hydrogen, chlorine, bromine and ($C_1$–$C_4$)alkyl; X is a substituent selected from the group consisting of hydrogen, ($C_1$–$C_4$)alkyl, halogen, cyano, aryl, hydroxy, carboxy, and OY groups wherein Y is an aryl group, as a vapor with chlorine at a temperature of between 250°C. and 750°C., condensing the organic reaction product and separating the halogenated reaction product from by-products formed therewith.

2. A continuous single step, vapor phase process for the preparation of a substituted vinylbenzyl chloride which comprises intermixing a substituted ethyltoluene of the formula:

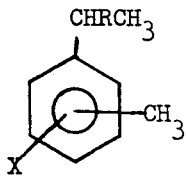

wherein R is a substituent selected from the group consisting of hydrogen, chlorine and bromine and X is a substituent selected from the group consisting of hydrogen, ($C_1$–$C_4$)alkyl, halogen, cyano, aryl, hydroxy, carboxy and OY groups wherein Y is an aryl group, as a vapor admixed with diluent, with chlorine admixed with diluent in the presence of an inert reaction surface at a temperature of between 450°C. to 750°C. for a period of from 0.05 to 10 seconds condensing the organic reaction product, adding a polymerization inhibitor and separating the halogenated reaction product from by-products formed therewith by distillation.

3. A process according to claim 2 in which each of the gaseous reactants is admixed with an inert diluent.

4. A process according to claim 3 wherein the diluent is steam.

5. A process according to claim 3 wherein the diluent is nitrogen.

6. A process according to claim 3 wherein the inert reaction surface consists of high purity silica particles having $T_m \approx 1500°C$.

7. A process according to claim 3 wherein the polymerization inhibitor is selected from the group consisting of o-nitrophenol, o-nitrocresol and t-butylcatechol.

8. A process according to claim 3 wherein the substituted vinylbenzyl chloride precursors recovered from a single pass through the reactor are recycled through the reactor.

9. A process according to claim 3 wherein the substituted ethyltoluene is selected from the group consisting of:
2-ethyltoluene, 3-ethyltoluene, 4-ethyltoluene,
2-ethyl-3-methyltoluene, 2-ethyl-4-methyltoluene,
2-ethyl-5-methyltoluene, 2-ethyl-6-methyltoluene,
3-ethyl-2-methyltoluene, 3-ethyl-4-methyltoluene,
3-ethyl-5-methyltoluene, 4-ethyl-2-methyltoluene,
4-ethyl-3-methyltoluene, 5-ethyl-2-methyltoluene,
2,3-diethyltoluene, 2,4-diethyltoluene,
2,5-diethyltoluene, 2,6-diethyltoluene,
3,4-diethyltoluene, 3,5-diethyltoluene,
2-(chloroethyl)toluene, 3-(chloroethyl)toluene,
4-(chloroethyl)toluene, 2-(chloroethyl)-3-methyltoluene, 2-(chloroethyl)-4-methyltoluene,
2-(chloroethyl)-5-methyltoluene, 2-(chloroethyl)-6-methyltoluene, 3-(chloroethyl)-2-methyltoluene,
3-(chloroethyl)-4-methyltoluene, 3-(chloroethyl)-5-methyltoluene, 4-(chloromethyl)-2-methyltoluene,
4-(chloroethyl)-3-methyltoluene, 5-(chloroethyl)-2-methyltoluene, 2,3-di(chloroethyl)toluene,
2,4-di(chloroethyl)toluene, 2,5-di(chloroethyl)toluene, 2,6-di(chloroethyl)toluene, 3,4-di(chloroethyl)toluene, 3,5-di(chloroethyl)toluene,
2-(bromoethyl)toluene, 3-(bromoethyl)toluene,
4-(bromoethyl)toluene 2-(bromoethyl)-3-methyltoluene,
2-(bromoethyl)-4-methyltoluene, 2-(bromoethyl)-5-methyltoluene, 2-(bromoethyl)-6-methyltoluene,
3-(bromoethyl)-2-methyltoluene, 3-(bromoethyl)-4-methyltoluene, 3-(bromoethyl)-4-methyltoluene,
3-(bromoethyl)-5-methyltoluene, 4-(bromoethyl)-2-methyltoluene, 4-(bromoethyl)-3-methyltoluene,
5-(bromoethyl)-2-methyltoluene, 2,3-di(bromoethyl)toluene, 2,4-di(bromoethyl)toluene, 2,4-di(bromoethyl)toluene, 2,5-di(bromoethyl)toluene, 2,6-di(bromoethyl)toluene, 3,4-di(bromoethyl)toluene,
3,5-di(bromoethyl)toluene.

10. A process according to claim 3 wherein an isothermal temperature is utilized in the reactor.

11. A process according to claim 3 wherein a gradient temperature is utilized in the reactor.

12. A process according to claim 3 wherein the substituted ethyltoluene is 4-ethyltoluene.

* * * * *